United States Patent
Mangat et al.

(12) 
(10) Patent No.: US 6,462,066 B2
(45) Date of Patent: Oct. 8, 2002

(54) METHOD AND COMPOSITION FOR TREATMENT OF ISCHEMIC NEURONAL REPERFUSION INJURY

(75) Inventors: Harpal S. Mangat, Bala Cynwyd; Gerry Ballough, Drexel Hill; Gary Brown, Flourtown, all of PA (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/727,707

(22) Filed: Dec. 4, 2000

(65) Prior Publication Data

US 2001/0053790 A1 Dec. 20, 2001

Related U.S. Application Data

(60) Provisional application No. 60/168,547, filed on Dec. 2, 1999.

(51) Int. Cl.⁷ .................... A61K 31/445; A61K 31/12
(52) U.S. Cl. ........................ 514/398; 514/681
(58) Field of Search ................. 514/398, 681

(56) References Cited

U.S. PATENT DOCUMENTS

| | | | |
|---|---|---|---|
| 4,439,196 A | 3/1984 | Higuchi | 604/890 |
| 4,447,224 A | 5/1984 | Decant, Jr. et al. | 604/67 |
| 4,447,233 A | 5/1984 | Mayfield | 604/152 |
| 4,486,194 A | 12/1984 | Ferrara | 604/897 |
| 4,487,603 A | 12/1984 | Harris | 604/152 |
| 4,925,678 A | 5/1990 | Ranney | 424/493 |
| 4,959,217 A | 9/1990 | Sanders et al. | 424/473 |
| 5,122,110 A | 6/1992 | McNally et al. | 600/36 |
| 5,145,769 A | 9/1992 | McNally et al. | 435/1 |
| 5,149,621 A | 9/1992 | McNally et al. | 435/1 |
| 5,158,867 A | 10/1992 | McNally et al. | 435/1 |
| 5,167,616 A | 12/1992 | Haak et al. | 604/20 |
| 5,169,383 A | 12/1992 | Gyory et al. | 604/20 |
| 5,225,182 A | 7/1993 | Sharma | 424/9 |
| 5,506,231 A | 4/1996 | Lipton | 514/289 |
| 5,597,809 A | 1/1997 | Dreyer | 514/37 |

FOREIGN PATENT DOCUMENTS

| | | |
|---|---|---|
| JP | 6-263636 | 9/1994 |
| WO | WO93/23082 | 11/1993 |
| WO | WO94/13275 | 6/1994 |
| WO | WO95/15958 | 5/1995 |
| WO | WO98/01099 | 1/1998 |
| WO | WO98/43612 | 10/1998 |
| WO | WO99/16741 | 4/1999 |
| WO | WO00/37089 | 6/2000 |

OTHER PUBLICATIONS

Scot E. Moss, et al., "Ocular Factors in the Incidence and Progression of Diabetic Retinopathy", Ophthalmology, vol. 101, No. 1, Jan. 1994, pp. 77–83.

Mangat, "Retinal Artery Occlusion", Surv Ophthalmol, vol. 40, No. 2, Sep.–Oct. 1995, pp. 145–156.

Lei, Sizheng Z. et al. *Blockade of NMDA Receptor–Mediated Mobilization of Intracellular $Ca^{2+}$ Prevents Neurotoxicity*, pp. 196–202, Elsevier Science Publishers B.V. 1992.

Tian, Qing et al. *Effects of Azumolene on Doxorubicin–Induced $Ca^{2+}$ Release From Skeletal and Cardiac Muscle Sarcoplasmic Reticulum*, pp. 27–34, Elsevier Science Publishers B.V. 1991.

Primary Examiner—Raymond Henley, III
(74) Attorney, Agent, or Firm—Saliwanchik, Lloyd & Saliwanchik

(57) ABSTRACT

Methods and compositions for treatment of, or protection from, neuropathy resulting from reperfusion injury upon reversal of an ischemic condition, comprising treatment or prophylactic treatment of the patient with an antagonist of the type 3 ryanodine receptor, such that a rise in cytosolic $Ca^{2+}$ concentration is prevented. Therapeutic compositions containing dantrolene or aminodantrolene are administered to the patient to prevent a rise in cytosolic $Ca^{2+}$ that would otherwise result in $Ca^{2+}$-mediated neuronal damage. Treatment of ischemic optic neuropathy by this method is shown, and the methods and compositions presented are also applicable to other ischemic reperfusion neuropathies, such as stroke, reperfusion injury after TPA treatment/carotid endarterectomy, seizures, and excitotoxic retinal damage in glaucoma.

16 Claims, 7 Drawing Sheets

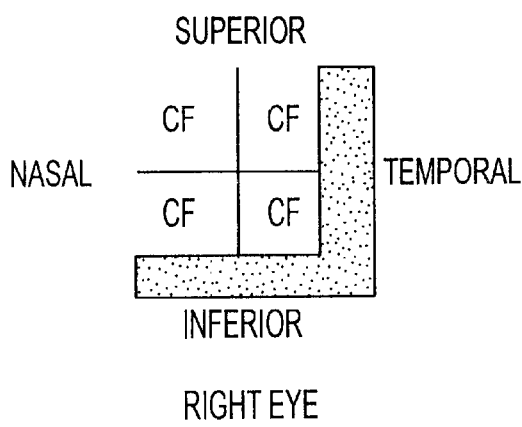
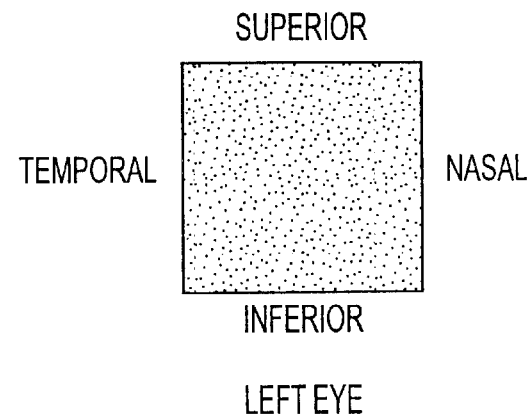
FIG. 2A
FIG. 2B
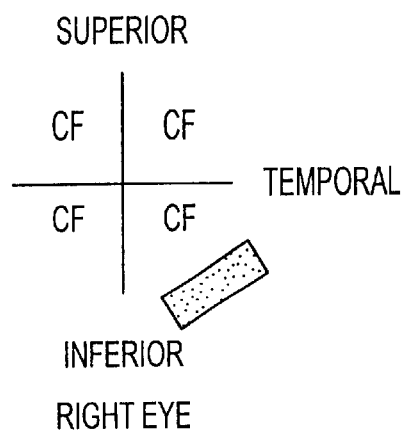
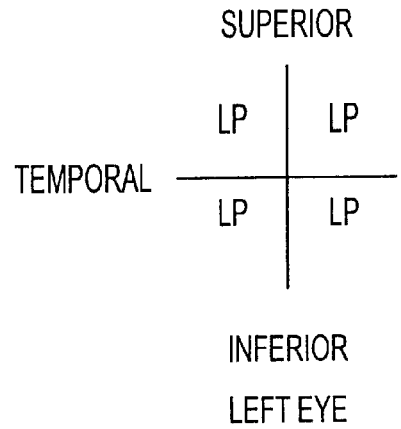
FIG. 3A-1
FIG. 3A-2

48 HOURS OF TREATMENT

72 HOURS OF TREATMENT

96 HOURS OF TREATMENT

24 HOURS AFTER STARTING DANTROLINE (RIGHT EYE)

```
                        PATTERN
                        DEVIATION
     RIGHT
     AGE    69                    -7 -20 | -2 -9
     FIXATION LOSSES    0/30   -13 -2 -1 |  1  2 -2
     FALSE POS ERRORS  0/26 -12 -5 -3 -1 | -3 -2 -1 -5
     FALSE NEG ERRORS  1/17 -7 -11 -1  2 -2 | -2 -1 -4 -7 -8
     QUESTIONS ASKED    621 -10 -2 -3 -1  2 |  1 -2     -5 -15
                            ─────────────── ───────────────
                            -8 -4  0 -1 -3 | -1  2     -5 -9
                            -5 -6 -3 -7 -1 | -1 -2 -1 -4 -20
                               -5  0 -4 -4 | -3 -3 -5 -8
                                  -10 -8 -3| -5 -7 -6
                                      -6 -13| -6 -5
```

GLOBAL INDICES
                                        MD   - 3.03 DB  P <  10%
                                        PSD    4.43 DB  P <   5%
                                        SF     1.34 DB
                                        CPSO   4.16 DB  P <   2%

FIG. 5A

PATTERN
     RIGHT              DEVIATION
     AGE    69
     FIXATION LOSSES    0/30
     FALSE POS ERRORS  0/26
     FALSE NEG ERRORS  1/17
     QUESTIONS ASKED    621

PROBABILITY SYMBOLS

:: P <  5%
        ✿ P <  2%
        ✸ P <  1%
        ■ P < 0.5%

GLOBAL INDICES
                                        MD   - 3.03 DB  P <  10%
                                        PSD    4.43 DB  P <   5%
                                        SF     1.34 DB
                                        CPSO   4.16 DB  P <   2%

FIG. 5B

```
           PATTERN
LEFT       DEVIATION
AGE  69                 3  3  | 6   6
FIXATION LOSSES  2/17
                    0  0 -1   | 5  10  23
FALSE POS ERRORS 0/8
FALSE NEG ERRORS 1/3 xx  -1 -2  3 -1 | -4  8 -3  23
QUESTIONS ASKED  269  -2 -3 -4 -5 -3 |  0  6 -4  6  11
                      -3  0    -6 -3 | -7 -7 -6 -3 -1
                      ─────────────────────────────
                         -4 -5 -6 -8 | -8 -7 -6 -4 -1
                      -3 -4 -5 -6 -7 | -7 -7 -5 -3 -1
                         -4 -5 -5 -5 | -5 -5 -4 -2
                            -3 -4 -4 | -4 -3 -2
                               -2 -2 | -2 -1
```

GLOBAL INDICES
                                        MD   -23.12 DB  P < 0.5%
                                        PSD    5.25 DB  P <  2%
                                        SF     3.60 DB  P <  2%
                                        CPSO   3.31 DB  P <  5%

FIG. 6A

PATTERN
LEFT       DEVIATION
AGE  69
FIXATION LOSSES  2/17
FALSE POS ERRORS 0/8
FALSE NEG ERRORS 1/3 xx
QUESTIONS ASKED  269

PROBABILITY SYMBOLS

∷ P <  5%
⋈ P <  2%
▨ P <  1%
■ P < 0.5%

GLOBAL INDICES
                                        MD   -23.12 DB  P < 0.5%
                                        PSD    5.25 DB  P <  2%
                                        SF     3.60 DB  P <  2%
                                        CPSO   3.31 DB  P <  5%

FIG. 6B

| VISUAL FIELDS | OS | OD |
|---|---|---|
| IMMEDIATELY AFTER SURGERY<br>NO LIGHT PERCEPTION | (fully shaded circle) | (fully shaded circle) |
| DAY 1 OF TREATMENT<br>VISUAL ACUITY WITH GLASSES<br>COUNT-FINGERS OU IN SUPERIOR FIELD | CF (top half clear, bottom half shaded) | CF (top half clear, bottom half shaded) |
| DAY 3 OF TREATMENT<br>CENTRAL ISLAND OF VISION,<br>VISUAL ACUITY VARYING FROM COUNT-FINGERS TO HAND MOTION | CF HM | HM HM |
| STRONGLY POSITIVE FOR RED/GREEN COLORATION<br>DAY 4 OF TREATMENT<br>PERCEIVES COLOR VISION | CF, HM (upper-right quadrant clear, others shaded) | HM (mostly shaded) |
| STRONGLY POSITIVE BLUE COLOR<br>DAY 5 OF TREATMENT<br>PERCEIVES BLUE COLOR | CF, HM (upper-right quadrant clear, others shaded) | HM |
| DAY 7 (2 DAYS OF NO TREATMENT)<br>VISUAL FIELD, COLOR PERCEPTION AND VISUAL ACUITY MAINTAINED 2 DAYS AFTER TREATMENT STOPPED | CF, HM | HM |

FIG. 7

METHOD AND COMPOSITION FOR TREATMENT OF ISCHEMIC NEURONAL REPERFUSION INJURY

This application claims benefit of U.S. Provisional Application No. 60/168,547 filed Dec. 2, 1999.

FIELD OF THE INVENTION

This invention relates to the treatment of neuropathy resulting from ischemic reperfusion injury in a mammal. Such neuropathies include, but are not limited to, optic ischemic neuropathy, stroke, reperfusion injury after TPA treatment or other lytic treatments/carotid endarterectomy, seizures, and excitotoxic retinal damage in glaucoma.

BACKGROUND OF THE INVENTION

When the blood supply to neural tissues such as brain or retina is interrupted, a complex series of biochemical changes begins which may result in neuronal cell damage. At the cellular level, it is known in the art that damage is mediated by opening of the N-methyl-D-aspartate channels in the membrane. Ischemia begins when the blood supply stops or is significantly slowed, and this phase may be followed by restoration of the blood supply during a reperfusion phase. It is well established that cellular damage may occur during both phases, though by different mechanisms. These processes and the mechanisms for damage are described in "Clinical Challenges. Retinal Artery Occlusion" H. S. Mangat, Survey of Ophthalmology 40, 145–156 (1995), which is incorporated in its entirety by reference herein.

The complex series of events known in the art to contribute to cell death during ischemia/reperfusion are summarized in FIG. 1 in diagrammatic form. FIG. 1 shows six substances that accumulate during ischemia: excitatory amino acids (1), intracellular calcium (2), arachidonic and other free fatty acids (3), hypoxanthine (4), xanthine oxidase (5), and platelet activating factor (6).

Ischemia triggers at least three pathways deleterious to the cell. Firstly, a lack of oxygen depletes energy stores (principally ATP), which disrupts homeostatic mechanisms, most importantly the membrane pump mechanism that maintains intracellular calcium at a low level. The resulting rise in intracellular calcium (2), which occurs principally because of the opening of the N-methyl-D-aspartate (NMDA) channels in the membrane, increases release of glutamic acid, activates destructive proteases and lipases (7), and indirectly converts the enzyme xanthine dehydrogenase (8) to the potentially harmful xanthine oxidase (5). Secondly, excitatory amino acids (1) ("excitotoxins"), principally glutamic and aspartic acids, are released, which activate calcium channels, further increasing intracellular calcium through a positive feedback mechanism, and allowing entry into the cell of excess water, sodium and chloride. Thirdly, acidosis enhances destructive lipid peroxidation and the release of damaging free radicals (9).

Upon restoration of the blood supply the reperfusion phase begins. The increased intracellular calcium level (2), a result of opened NMDA channels during ischemia, may now trigger a more destructive cascade. The initial calcium impulse causes a cascade that results in the release of intracellular calcium stores from the intravesicular calcium deposit. The release of intracellular calcium is mediated via the ryanodine receptor, principally the type 3 ryanodine receptor. The net result is a thirtyfold rise in intracellular calcium and cell death. Attempts have been made to reperfuse as soon as possible after the onset of ischemia, but it is important to note that the reperfusion itself causes the cascade, therefore the neurodestructive phases of ischemia and reperfusion are distinct.

Neurophysiologists now view reperfusion injury as a cascade process that leads to excitotoxic cell death. The rise in intracellular calcium during reperfusion causes vasoconstriction of neighboring blood vessels. In addition, it causes the release of free oxygen radicals (9), in part from the action of xanthine oxidase (5). The net result is excitotoxic neuronal cell death (10).

Ryanodine Receptor Antagonists

Increased cytosolic $Ca^{2+}$ concentration contributes significantly to neuronal cell damage during ischemic reperfusion. It is desirable to prevent or minimize ischemic neuronal reperfusion injury; that is, to prevent or minimize neuronal cell damage that occurs during the reperfusion phase of an ischemic episode.

Dantrolene is an antagonist of the type 3 ryanodine receptor and is commonly given as the sodium salt (sodium dantrium), which is hydrated 1-[[[5-(4-nitrophenyl)2-furanyl]methylene]amino]-2,4-imidazolidinedione sodium salt. Dantrolene is prescribed in the treatment of clinical spasticity resulting from upper motor neuron disorders such as spinal chord injury, cerebral palsy, stroke, or multiple sclerosis. Dantrolene is also effective in reversing the hypermetabolic process of malignant hyperthermia, a genetic disorder of skeletal muscle that is triggered by exposure to anesthetics and certain relaxants.

Other therapeutic uses for dantrolene are known in the art. For example, Dreyer, U.S. Pat. No. 5,597,809, teaches the use of NMDA-receptor antagonists, and also dantrolene, for the treatment of optic neuritis. U.S. Pat. No. 5,506,231 to Lipton teaches the use of dantrolene for the treatment of three conditions specifically associated with AIDS: dementia, myelopathy, and blindness. Dantrolene has been used clinically to treat malignant hypothermia, as it is known to reduce cellular energy requirements, creating a hypothermic environment. Kiyoshi (Patent Abstracts of Japan (1994), publication number 06263636) discloses the use of dantrolene for treatment of cerebral nerve diseases such as geriatric dementia, Parkinsons disease and Huntingtons disease.

Non-therapeutic uses for dantrolene include cryopreservation of blood vessels. See U.S. Pat. Nos. 5,158,867; 5,149,621; 5,145,769 and 5,122,110.

Ischemic Optic Neuropathy

Ischemic optic neuropathy (ION) is a distinct condition from optic neuritis (ON), and ION is distinguished from ON by several diagnostic criteria. Typically, ION patients are 60 years or older, while ON affects younger patients for whom 40 years is the typical age of onset. A key event in the development of ION pathology is ischemia, whereas inflammation is essential to the pathology of ON. In the majority of cases, ION is a painless condition. In contrast, ON is reported to be very painful. Finally, and most significantly to the present invention, the visual acuity lost by a patient having ON is recovered in the majority (71%) of cases. In contrast, for the vast majority of ION patients, loss of visual acuity is permanent and spontaneous recovery is very rare. See American Academy of Ophthalmology (1994) pp.76–83. It is therefore desirable to prevent or minimize the loss of visual acuity.

DESCRIPTION OF THE FIGURES

FIGS. 2A and 2B illustrate left-and right-eye optical fields, examined post-operatively in the patient of Example 1.

FIGS. 3A-1 and 3A-2 illustrate the confrontational visual fields, 24 hours postoperatively, of the patient of Example 1.

FIGS. 5A and 5B show visual field test results approximately four months postoperatively for the right eye of the patient of Example 1.

FIGS. 6A and 6B show visual field test results approximately four months postoperatively for the left eye of the patient of Example 1.

FIG. 7 illustrates progression of the visual fields of both eyes of the patient of Example 2.

BRIEF SUMMARY OF THE INVENTION

Figure 1:
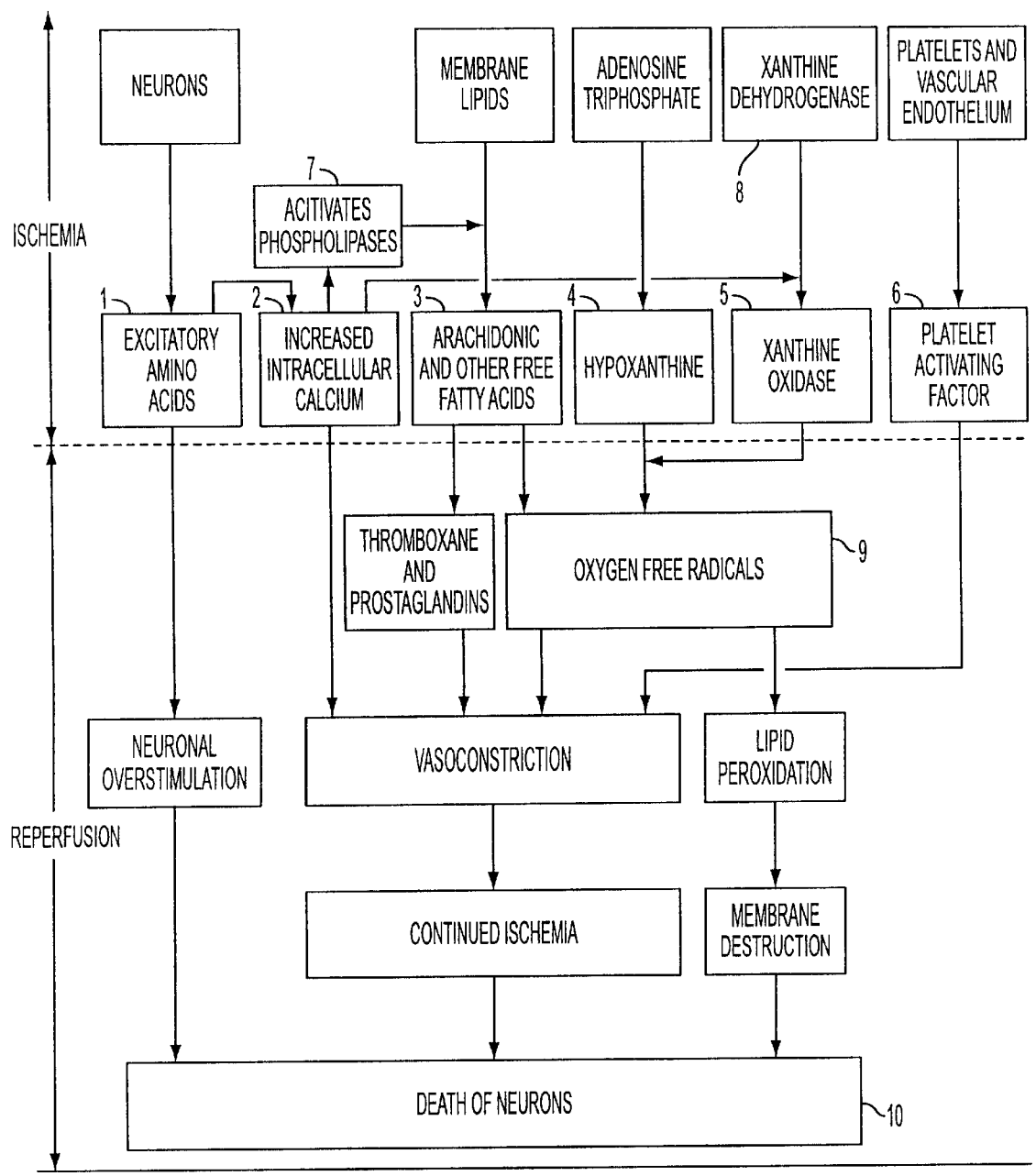
FIG. 1 is a schematic representation of metabolic pathways involved in ischemic and reperfusion injury to neurons. The six boxes (1–6) immediately above the broken line represent increased concentrations of metabolites, which are formed during the ischemic period but do not cause their damaging effects until they are metabolized during the period of reperfusion injury. Metabolic events during reperfusion are depicted below the broken line, and may lead to cell death.

It is therefore an object of the present invention to provide a method and compositions for the treatment of patients with an ischemic neuropathy, including, for example, ischemic optic neuropathy, ischemic retinopathy, stroke, reperfusion injury after TPA treatment, reperfusion injury after carotid endoarterectomy, seizures, or excitotoxic retinal damage in glaucoma.

It is a further object of the invention to provide methods and compositions for inhibiting the rise in intracellular $Ca^{2+}$ concentration that occurs upon reperfusion following an ischemic event. In one embodiment, antagonists of the type 3 ryanodine receptor, including but not limited to pharmaceutically acceptable salts of dantrolene, aminodantrolene, and mixtures of same, are administered to block cytoplasmic influx of $Ca^{2+}$, and thereby prevent or minimize neuronal reperfusion injury.

It is a still further object of the present invention to prevent ischemic reperfusion injury in a mammal by the administration of pharmaceutically acceptable salts of dantrolene, aminodantrolene, and mixtures of same.

In further embodiments, azumolene, cyclopiazonic acid, 2,5-di(tert butyl)-1,4-benzohydroquinone, or mixtures thereof, are used to prevent ischemic reperfusion injury in a mammal.

Another object of the present invention is to prevent ischemic retinopathy in a non-human mammal or a human patient by administering a compound that inhibits intracellular calcium-mediated retinal cell damage, including pharmaceutically acceptable salts of dantrolene, aminodantrolene, and mixtures of same.

Dantrolene, aminodantrolene, or an equivalent antagonist of the ryanodine receptor, preferably an inhibitor of the type 3 ryanodine receptor, is used, alone or in combination, to prevent or treat neuropathy resulting from reperfusion of ischemic neuronal tissue in a mammal. Treatment prevents intracellular release of $Ca^{2+}$ stores, which prevents or ameliorates neuronal damage that otherwise may occur upon reperfusion.

These and other objects of the present invention will become obvious to those skilled in the art upon review of the following disclosure.

DETAILED DESCRIPTION OF THE INVENTION

It is desirable to treat neuronal reperfusion injury by blocking the calcium-triggered cascade that releases intracellular calcium stores. This is accomplished in the present invention by blocking the cascade at a point that is different from that of the so-called NMDA-blockers, such as memantine, that are currently used or in development to treat the ischemic phase of neuropathy. Ryanodine type 3 receptor antagonists such as dantrolene or aminodantrolene, or their functional equivalents, are instead used to block the release of intracellular calcium stores during reperfusion.

Drugs that can be used in the present invention include dantrolene, aminodantrolene, and azumolene. Other compounds that also inhibit intracellular calcium release, and which may be used in the present invention, are cyclopiazonic acid (thapsaigargin), and BHQ [2,5-di(tert butyl)-1,4-benzohydroquinone].

The following two examples illustrate the preferred embodiment of the instant invention, in which dantrolene is used to successfully treat two patients with optic ischemic neuropathy caused by anesthesia.

METHODS

The compounds of the present invention are drugs that prevent release of intracellular calcium by antagonism of the ryanodine receptor. These drugs are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including, but not limited to, improved survival rate, or more rapid recovery, or improvement or elimination of symptoms and other indicators as are selected as appropriate measures by those skilled in the art.

In the method of the present invention, the compound of the present invention can be administered in various ways. It should be noted that it can be administered as the compound or as a pharmaceutically acceptable salt and can be administered alone or as an active ingredient in combination with pharmaceutically acceptable carriers, diluents, adjuvants and vehicles. The compounds can be administered orally, subcutaneously, parenterally, intravenously, intraarterialy, intramuscularly, intraperitoneally, intranasally, intrathecally and via infusion techniques. Implants of the compound are also useful. The patient being treated is a mammal and, in particular, mammals including man. The pharmaceutically acceptable carriers, diluents, adjuvants and vehicles, as well as implant carriers generally refer to inert, non-toxic solid or liquid fillers, diluents or encapsulating material not reacting with the active ingredients of the invention.

The doses may be single doses or multiple doses over a period of several days. The treatment generally has a length dependent upon the length of the disease process, drug effectiveness and the patient species being treated.

When administering the compound of the present invention parenterally, it will generally be formulated in a unit dosage injectable form (solution, suspension or emulsion). The pharmaceutical formulations suitable for injection include sterile aqueous solutions or dispersions, and sterile powders for reconstitution into sterile injectable solutions or dispersions. The carrier can be a solvent or dispersing medium containing, for example, water, ethanol, polyol (for example glycerol, propylene, glycol, liquid polyethylene glycol, and the like), suitable mixtures thereof, and vegetable oils.

Proper fluidity can be maintained, for example, by the use of a coating such as lecithin, by the maintenance of the required particle size in the case of a dispersion, and by the use of surfactants. Non-aqueous vehicles such as cottonseed oil, sesame oil, olive oil, soybean oil, corn oil, sunflower oil, or peanut oil and esters, and isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Contamination by microorganisms can be avoided by the use of various antibacterial and antifungal agents, for example parabens, chlorobutanol, phenol, sorbic acid, and the like. In many cases, it will be desirable to include isotonic agents, for example sugars, sodium chloride, and the like. Prolonged absorbtion of the injectable pharmaceutical form can be brought about by the use of agents delaying absorbtion, for example, aluminum monostearate and gelatin. Any vehicle, diluent, or additive selected is compatible with the compounds.

Sterile injectable solutions can be prepared by incorporating the compounds utilized in practicing the present invention in the required amount of the appropriate solvent with various other ingredients as desired.

A pharmacological formulation of the present invention can be administered to the patient in an injectable formulation containing any compatible carrier, such as various vehicles, adjuvants, additives, and diluents. Alternatively, the compound utilized in the present invention can be administered parenterally to the patient in the form of slow-release subcutaneous implants or targeted delivery systems, such as monoclonal antibodies, vectored delivery, iontopheric delivery, polymer matrices, liposomes, and microspheres. Examples of delivery systems useful in the present invention include U.S. Pat. Nos. 5,225,182; 5,169, 383; 5,167,616; 4,959,217; 4,925,678; 4,487,603; 4,486, 194; 4,447,233; 4,447,224; and 4,439,196, each herein incorporated in its respective entirety. Many alternative implants, delivery systems, and modules are well known to those of skill in the art.

A pharmacological formulation of the compound utilized in the present invention can be administered orally to the patient. Conventional methods, such as administering the compounds in tablets, suspensions, solutions, emulsions, capsules, powders, syrups, and the like are usable. Known techniques, which deliver the compound orally or intravenously and retain the biological activity, are preferred.

In one embodiment, the compound of the present invention can be administered initially by intravenous injection to bring blood levels to a suitable level. The patient's blood levels are than maintained by an oral dosage form, although other forms of administration, dependent upon the patient's condition and as indicated above, can be used. The quantity to be administered will vary for the patient being treated, and will vary from about 100 ng/kg of body weight to 100 mg/kg of body weight per day, and preferably will be from 10 $\mu$g/kg to 10 mg/kg per day. However, as shown in Example 1, the 1–2 mg/kg body weight as a loading dose is preferred, followed by 1–2 mg/kg every two hours three times, then every 8 hours until the ischemic condition resolves. For glaucoma, neuroprotective daily doses of approximately 0.1 mg/kg can be used. In general, sub-toxic doses as set forth in *Physicians Desk Reference*, $42^{nd}$ edition (1988), are preferred. Methodology to determine dosing as set forth in U.S. Pat. No. 5,597,809 can also be used.

EXAMPLE 1

A female patient undergoes back surgery lasting 8 hours and, upon awakening after 16 hours, complains of not being able to see from her left eye. The surgery had lasted 8 hours, and 1 unit of blood had been lost. During surgery, her systolic blood pressure had dropped to 80 mm Hg. She has a long-standing history of hypertension, and subsequent evaluation reveals that she has sustained a myocardial infarction. She is a contact lens wearer. previously having a corrected visual acuity of 20/20 bilaterally.

Post-operative opthalmic examination reveals an uncorrected visual field of 20/70 in the right eye, and no perception of light in the left eye. There is a relative afferent pupillary defect on the left. She has a sizeable loss of her right visual field, which is illustrated in FIGS. 2A and 2B. Dilated fundus examination shows bilateral pale optic discs with venous pulsations on the right. Both pupils are reactive, varying in diameter from 3.0 to 3.5 mm. The confrontational visual fields on initial exam are shown in FIGS. 2A and 2B.

Her extra-ocular muscle movements, intraocular pressures, and anterior segment exam, are within normal limits. Fundus exam shows a pale optic disc with a cup-to-disc ratio of 0.4 in the left eye. The right optic disc is of normal color. However, the superior opthalmic vein is loose from its fibrous attachments to the optic disc. It is pulsatile, and each time a pulse occurs, it jumps away from the optic disc. This can be clearly seen with a 90 diopter lens and a portable Kowa slit lamp, or with a 20 diopter lens and a Keeler indirect opthalmoscope. The retina appears normal in both eyes. A clinical diagnosis in the left eye of posterior ischemic optic neuropathy resulting in no light perception is made. A clinical diagnosis of posterior ischemic optic neuropathy with resultant field defect and pending loss of vision in the right eye is also made. MRI of the optic nerves confirms these diagnoses. Bilateral swelling of the optic nerves is seen behind the optic discs. The swelling is more marked in the left optic nerve than in the right. MRI confirms that she has a swollen optic left nerve. A diagnosis of bilateral ischemic optic neuropathy is made: the blood supply to the left eye has been occluded, and the same process is occurring in the right eye. Just prior to discovering her loss of sight, her serum calcium is low, and the nurse administers intravenous calcium.

To prevent compression of the blood supply in the right eye, the patient is given high dosed pulsed steroids. However, excitotoxic damage of the retina from reperfusion injury is almost certain in the absence of the treatment of the present invention. Therefore, to prevent reperfusion injury dantrolene is administered as per the present invention, since it is known that dantrolene prevents excitotoxic damage in an animal seizure model.

The patient is administered 2 gm solumedrol, and then 1 gm every 6 hours. Dantrolene is administered at 2 mg/kg every 2 hours for three treatments, and then 1 mg/kg every 8 hours. She is re-examined 24 hours later and her corrected visual acuity in the right eye is 20/30, while the left eye has light perception. Her confrontational visual fields are shown in FIGS. 3A-1 and 3A-2.

Figure 3B:
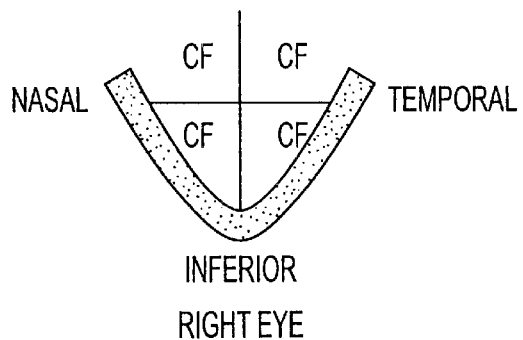
FIG. 3B illustrates the right eye confrontational visual field, 24 hours postoperatively, in response to a red top.
Figure 4A:
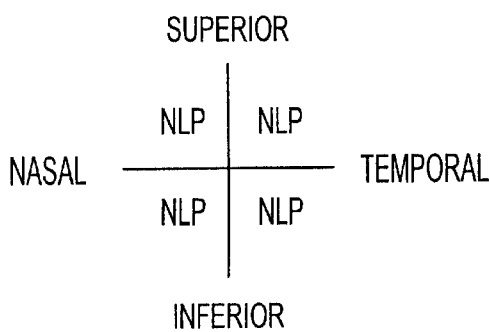
FIGS. 4A through 4F illustrate progression of the visual field of the left eye of the patient of Example 1.
Figure 4B:
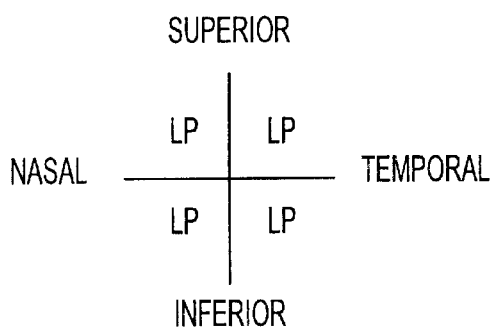
Figure 4C:
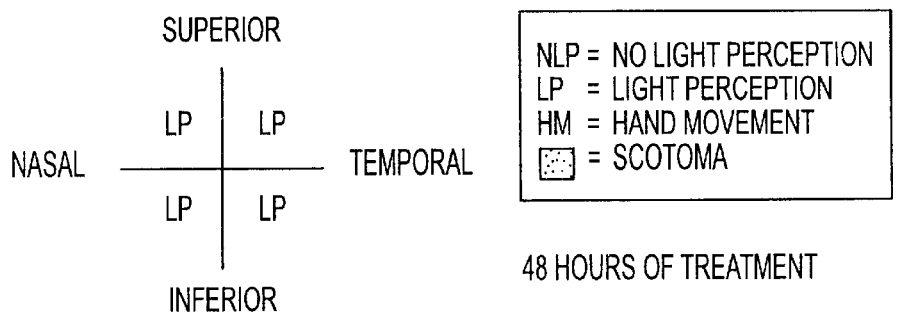
Figure 4D:
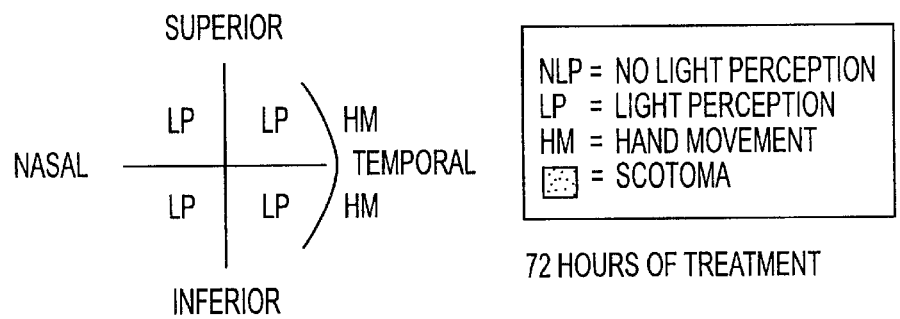
Figure 4E:
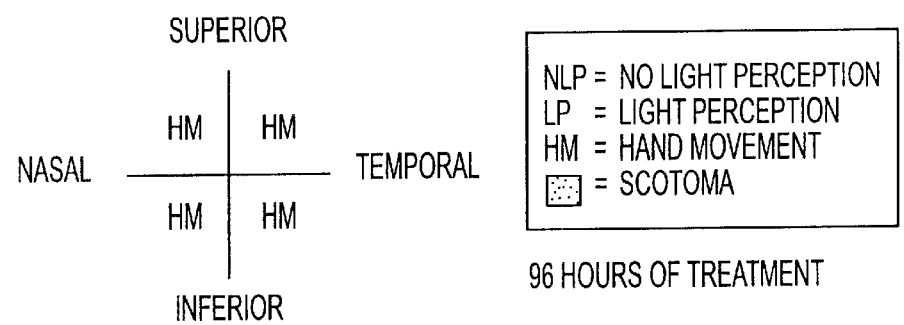
Figure 4F:
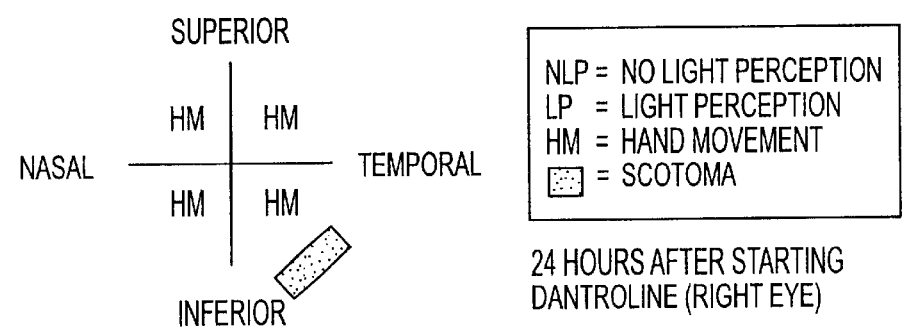

Her confrontational visual fields at 24 hours, in response to a red top in the right eye, are shown in FIG. 3B, and show a significant scotoma to red top.

A scotoma to fingers (initial scotoma at 24 hours) reflects impending neuronal death of the visual pathway that detects that field. At this time, the scotoma is in the inferotemporal field only, indicating that the neural pathway of the superior nasal retina to the brain is affected. The red top scotoma matched the scotoma at the initiation of treatment.

Example 1 illustrates the action of dantrolene acts as a neuroprotective agent against reperfusion injury. The inferior field loss lessens 48 hours after starting treatment and continues until there is none at the fifth day. However, the scotoma to red top remains, indicating that an ischemic insult has occurred to the corresponding neurons. Her uncorrected visual acuity returns to 20/50 in the right eye by the fifth day.

The initial restoration of light perception in the left eye 24 hours after initiation of treatment continues to improve. At 72 hours after treatment she starts to perceive hand movement. Her progressive visual field movements are documented in FIGS. 4A–4F.

The fields show that dantrolene prevents reperfusion injury. As reperfusion of the left optic nerve is established, the visual acuity and quality of the field improves from no light perception to hand movement. This illustrates that intervention at a time of no light perception helps to protect those neurons that have not yet been damaged, so that they are functional to produce hand-movement vision.

Two months after discharge, the woman is re-examined. She states that she sees "beautiful colors in orange light" with her right eye. She continues to have a direct relative afferent pupillary defect in her left eye. Her corrected visual acuity in the left eye is counting fingers at distance and 20/800 at near distance. Her optic disc photographs and visual fields to both white and red test objects are shown. She maintains her scotoma to red light as described above. This scotoma is absent in the white object visual field.

FIGS. 5A–B and 6A–B show subsequent visual field test results (Macular Field Test: Central 30-2 Threshold Test) for the left and right eyes, respectively, showing the results of the therapy and the return of the patient's visual fields, and thus illustrating the efficacy of the present invention.

EXAMPLE 2

A 64-year-old white male awakes, after an L2-S1 posterior fusion with laminectomy operation, with no light perception in either eye. His past medical history is significant for an episode of hyperglycemia approximately 45 years previously. He has been a non-smoker for the last 20 years, and prior to that he was a heavy smoker.

The operation lasts for approximately 10 hours. He is under general anesthesia for the duration of the operation. The estimated blood loss is 2200 mL during the operation, of which 1200 mL is replaced via a cell saver, and an additional 2 units of blood is given along with crystalloids. His blood pressure drops once during the operation to 89 mm Hg. Before the surgery he is able to read with glasses. Opthalmic examination, subsequent to the operation, reveals no light perception in either eye, normal versions and ductions with pupils varying from 2 to 5 mm with no relative afferent pupilary defect in either eye. Anterior segment examination is normal, posterior segment examination reveals bilateral pale optic dics that are more marked on the left than the right. Strong venous pulsations are seen at the optic disc of the left eye. A diagnosis of bilateral ischemic optic neuropathy is made.

He is placed on intravenous dantrolene, 2 mg/kg body weight q 2 hourly×3 followed q 8 hourly. In addition, he is placed on solumedrol, 250 mg q 6 hourly. When he is reviewed 16 hours postoperatively, the visual acuity with glasses is counting fingers OU in the superior visual fields. His visual acuity fields are recorded on a daily basis. On day 3 his dantrolene treatment is changed from intravenous to oral 500 mg po tid. On day 4 color vision is restored and on day 5 all treatment is stopped.

The progression of his visual fields for both eyes is illustrated in FIG. 7.

The serum level of dantrolene is $14 \times 10^{-6}$ gm/mL on day 4, and $15 \times 10^{-6}$ gm/mL on day 2.

Example 2 illustrates that dantrolene serves as a neuroprotective agent, preventing visual loss once ischemia has set in, as exemplified by restoration of the superior visual fields and count fingers vision in both eyes.

Dantrolene treatment also prevents the effects of reperfusion injury as demonstrated by maintenance of the visual field and restoration of the color vision.

Throughout this application, various publications, including United States patents, have been referred to. The disclosures of these publications and patents in their entireties are hereby incorporated by reference into this application to more fully describe the state of the art to which this invention pertains.

While the invention has been described in terms of various preferred embodiments, those skilled in the art will recognize that various modifications, substitutions, omissions, and changes may be made without departing from the spirit of the present invention. Accordingly, it is intended that the scope of the present invention be limited solely by the scope of the following claims.

What is claimed is:

1. A method of treatment of neuronal reperfusion injury in a patient with ischemic neuropathy, said method comprising:
administering to said patient an effective amount of a therapeutic composition comprising a compound that decreases cytosolic $Ca^{2+}$ concentration caused by said reperfusion injury, and a pharmaceutically acceptable carrier.

2. The method of claim 1, in which said compound is an antagonist of type 3 ryanodine receptor.

3. The method of claim 2, wherein said compound is dantroline, aminodantroline, pharmaceutically acceptable salts thereof, or mixtures thereof.

4. The method of claim 1, wherein said neuropathy is ischemic optic neuropathy, ischemic retinopathy, stroke, reperfusion injury after TPA treatment, reperfusion injury after carotid endoarterectomy, seizures, excitotoxic retinal damage in glaucoma, or a combination thereof.

5. A method for decreasing reperfusion damage to the retina of a patient, said method comprising:
administering to said patient an effective amount of a therapeutic composition comprising a pharmaceutically acceptable carrier and a pharmaceutically acceptable salt of a compound, wherein said compound is an antagonist of type 3 ryanodine receptor and wherein said compound reduces the increase in cytosolic $Ca^{2+}$ concentration incident to said reperfusion injury.

6. The method of claim 5, in which said receptor antagonist is a pharmaceutically acceptable salt of dantrolene, aminodantrolene, or a mixture thereof.

7. A method of treatment of ischemic retinopathy reperfusion injury in a mammal, said method comprising: administering to said mammal a protective agent which inhibits intracellular calcium-mediated retinal cell damage, in a pharmaceutically acceptable carrier.

8. The method of claim 7, in which said protective agent is a pharmaceutically acceptable salt of dantrolene, aminodantrolene, or a mixture thereof.

9. A method of preventing ischemic neuropathy reperfusion injury in a mammal, said method comprising:
   administering to said mammal a pharmaceutically acceptable salt of dantrolene, aminodantrolene, or a mixture thereof.

10. A method of reducing reperfusion damage in a patient suffering from, or at risk of, ischemia, comprising:
   administering to said patient an effective amount of a therapeutic composition comprising a pharmaceutically acceptable carrier and a pharmaceutically acceptable salt of a compound, wherein said compound inhibits the intracellular release of calcium ions.

11. The method of claim 10, in which said compound is dantrolene, aminodantrolene, or a mixture thereof.

12. The method as in claim 1 in which said compound is azumolene, cyclopiazonic acid, 2,5-di(tert butyl)-1,4-benzohydroquinone, or mixtures thereof.

13. The method as in claim 2, in which said compound is azumolene, cyclopiazonic acid, 2,5-di(tert butyl)-1,4-benzohydroquinone, or mixtures thereof.

14. The method as in claim 5, in which said compound is azumolene, cyclopiazonic acid, 2,5-di(tert butyl)-1,4-benzohydroquinone, or mixtures thereof.

15. The method as in claim 10, in which said compound is azumolene, cyclopiazonic acid, 2,5-di(tert butyl)-1,4-benzohydroquinone, or mixtures thereof.

16. The method as in claim 7, wherein said protective agent is azumolene, cyclopiazonic acid, 2,5-di(tert butyl)-1,4-benzohydroquinone, or mixtures thereof.

* * * * *

UNITED STATES PATENT AND TRADEMARK OFFICE
CERTIFICATE OF CORRECTION

PATENT NO. : 6,462,066 B2 Page 1 of 1
DATED : October 8, 2002
INVENTOR(S) : Harpal S. Mangat, Gerry Ballough and Gary Brown It is certified that error appears in the above-identified patent and that said Letters Patent is hereby corrected as shown below:

Column 2,
Line 21, "1-[[[5-4(4-nitrophenyl)2-furanyl]methylene]amino]-2,4-imidazolidinedione" should read -- 1-[[[5-(4-nitrophenyl)-2-furanyl]methylene]amino]-2,4-imidazolidinedione --.

Column 5,
Line 43, "4,447,224; and4,439,196, each herein" should read -- 4,447,224; and 4,439,196, each herein --.

Signed and Sealed this

Twentieth Day of January, 2004

JON W. DUDAS
*Acting Director of the United States Patent and Trademark Office*